(12) United States Patent
Chiba et al.

(10) Patent No.: US 7,625,519 B2
(45) Date of Patent: Dec. 1, 2009

(54) METHOD FOR MANUFACTURING BIOMEDICAL POROUS ARTICLE

(75) Inventors: Akihiko Chiba, 13-12, Kitamatsuzono 1-chome, Morioka-shi, Iwate-ken (JP); Yoshiki Ono, Yokohama (JP); Masashi Sakamoto, Yokohama (JP); Akira Yamazaki, Yokohama (JP); Yoichi Nishio, Osaka (JP); Kenichi Omori, Tokyo-to (JP)

(73) Assignees: Akihiko Chiba, Morioka-shi (JP); NHK Spring Co., Ltd., Yokohama-shi (JP); Kobayashi Pharmaceut Ical Co., Ltd., Osaka-shi (JP)

( * ) Notice: Subject to any disclaimer, the term of this patent is extended or adjusted under 35 U.S.C. 154(b) by 401 days.

(21) Appl. No.: 11/104,647

(22) Filed: Apr. 13, 2005

(65) Prior Publication Data

US 2005/0254985 A1    Nov. 17, 2005

(30) Foreign Application Priority Data

Apr. 14, 2004 (JP) .............................. 2004-119185

(51) Int. Cl.
    *B22F 3/12* (2006.01)
    *A61F 2/02* (2006.01)
(52) U.S. Cl. ................. 419/2; 419/4; 419/6; 623/23.54
(58) Field of Classification Search ...................... 419/2, 419/4, 24, 6; 623/23.54
    See application file for complete search history.

(56) References Cited

U.S. PATENT DOCUMENTS

| 3,087,233 | A | * | 4/1963 | Turnbull | ...................... 428/605 |
| 3,278,279 | A | * | 10/1966 | Kraft et al. | .................. 428/605 |
| 3,432,295 | A | * | 3/1969 | Barr et al. | ...................... 419/19 |
| 3,887,365 | A | * | 6/1975 | Sherfey | ......................... 419/2 |
| 4,446,579 | A | | 5/1984 | Inamori et al. | ................. 3/1.91 |
| 4,570,271 | A | * | 2/1986 | Sump | ......................... 128/898 |
| 4,660,755 | A | | 4/1987 | Farling et al. | ............... 228/178 |
| 4,693,721 | A | * | 9/1987 | Ducheyne | ................ 623/23.54 |
| 5,013,324 | A | | 5/1991 | Zolman et al. | ................. 623/23 |
| 5,018,285 | A | | 5/1991 | Zolman et al. | ................. 29/465 |
| 5,496,372 | A | | 3/1996 | Hamamoto et al. | ........... 623/16 |
| 5,732,469 | A | | 3/1998 | Hamamoto et al. | ........ 29/896.6 |
| 6,063,332 | A | * | 5/2000 | Imamura et al. | ............... 419/4 |
| 6,240,616 | B1 | * | 6/2001 | Yan | ........................... 29/527.2 |
| 2004/0221926 | A1 | * | 11/2004 | Chiba et al. | ................. 148/425 |

FOREIGN PATENT DOCUMENTS

| JP | 4-141163 | 5/1992 |
| JP | 6-14943 | 3/1994 |
| JP | 07-184987 | 7/1995 |
| JP | 2002-363675 | 12/2002 |
| JP | 3544550 | 4/2004 |

OTHER PUBLICATIONS

Japanese Office Action dated Jun. 10, 2009, with English Translation.

* cited by examiner

*Primary Examiner*—Roy King
*Assistant Examiner*—Ncoclan T Mai
(74) *Attorney, Agent, or Firm*—Kratz, Quintos & Hanson, LLP (57) ABSTRACT

The present invention provides a method for manufacturing a biomedical porous article wherein communicability between the pores in the porous article is ensured and a desired porosity can be easily obtained, the method comprising a plate-like thread cluster formation step in which a plate-like thread cluster is obtained by dispersing many metallic threads made of a biomedical metallic material along a flat surface and entangling them; a compressing step of compressing the plate-like thread cluster into a desired thickness; and a sintering step of sintering the plate-like thread cluster.

8 Claims, 6 Drawing Sheets

METHOD FOR MANUFACTURING BIOMEDICAL POROUS ARTICLE

BACKGROUND OF THE INVENTION (1) Field of the Invention

The present invention relates to a method for manufacturing a porous article for in vivo use.

(2) Description of the Related Art

Porous articles for in vivo use are suitably used as a substitute prosthetic material for hard tissues such as bones and joints. Porous articles are fixed in the body by allowing osseous tissues, etc., to enter therein. Ceramics, polymers, etc., are known raw materials for the porous articles usable in vivo (i.e., biomedical porous articles). From the viewpoint of improving mechanical properties such as strength, ductility, etc., stainless steel, cobalt-chromium alloys, pure titanium, titanium alloys and like biocompatible metallic materials are also widely used.

Examples of known methods for manufacturing a biomedical porous article comprising such a metallic material include: forming a porous article by spraying and depositing titanium powder or the like onto a base material under high temperature and high pressure; obtaining a porous article by sintering a metallic material formed into bead-like shapes to evaporate a binder therein; obtaining a porous article by removing or deforming a portion of a metal base material by etching or blasting. However, since connections between pores cannot be obtained in porous articles obtained by these methods, if such a porous article is used as a bone prosthetic material, osseous tissues can barely enter the porous article, and therefore satisfactory linkage between the porous article and the bone cannot be obtained.

To overcome this problem, Japanese Unexamined Patent Publication No. 1995-184987 discloses a porous article wherein a plurality of metallic thin plates each having many pores are laminated, and the plurality of metallic thin plates are adhered to one another by heating. In this porous article, it is possible to control the alignment of pores by positioning the metallic thin plates while putting one on top of another. Therefore, a strong linkage between the porous article and tissues can be obtained by accelerating introduction of osseous tissues, etc., into the porous article.

However, in the porous article disclosed in Japanese Unexamined Patent Publication No. 1995-184987, positioning of the metallic thin plates while laminating is complicated and there is a risk of the metallic thin plates separating. Furthermore, in order to vary the porosity, additional metallic thin plates having different pore formation patterns must be prepared, and thus there is scope for improvement.

BRIEF SUMMARY OF THE INVENTION

The present invention was accomplished for overcoming the above-described problem.

An object of the present invention is to provide a method for manufacturing a biomedical porous article wherein a desired porosity can be easily obtained while ensuring communicability between the pores.

The object of the present invention can be achieved by a method for manufacturing a biomedical porous article comprising a plate-like thread cluster formation step in which a plate-like thread cluster is obtained by dispersing many metallic threads made of a biomedical metallic material along a flat surface and entangling them; a compressing step of compressing the plate-like thread cluster into a desired thickness; and a sintering step of sintering the plate-like thread cluster.

In this method for manufacturing a biomedical porous article, the compressing step is conducted in such a manner that a plurality of plate-like thread clusters are laminated and then compressed so as to have a desired total thickness. In this case, the plurality of plate-like thread clusters may include at least two types of the plate-like thread cluster of different volume fractions.

Furthermore, the compressing step and the sintering step may be simultaneously conducted in a same step.

An object of the present invention can also be achieved by a method for manufacturing a biomedical porous article comprising a plate-like thread cluster formation step in which a plate-like thread cluster is obtained by dispersing many metallic threads made of a biomedical metallic material along a flat surface and entangling them; a winding step of winding the plate-like thread cluster into a roll; and a sintering step of sintering the wound plate-like thread cluster.

In these methods for manufacturing a biomedical porous article, the metallic thread is formed from a Co—Cr—Mo alloy composed of 26-31 mass % of Cr, 8-16 mass % of Mo, with the balance being Co and impurities, and the metallic thread can be obtained from a metallic wire having a diameter of 20-200 µm. It is preferable that the length of the metallic thread be 1-1000 cm.

DETAILED DESCRIPTION OF THE INVENTION

Figure 1:
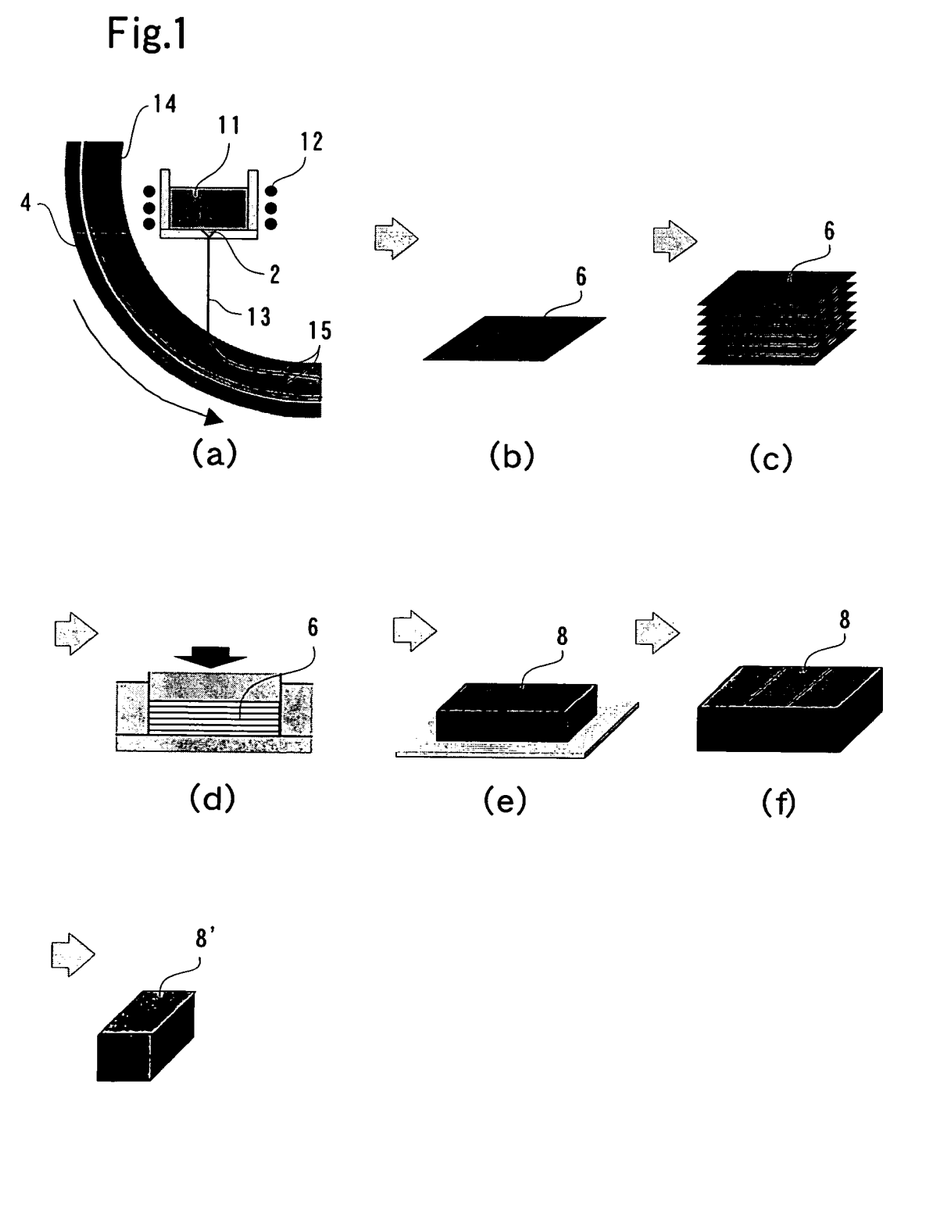
FIG. 1 is a process drawing explaining a method for manufacturing a biomedical porous article of one embodiment of the present invention.

Embodiments of the present invention are explained below with reference to drawings. FIG. 1 is a process drawing explaining a method for manufacturing a biomedical porous article of one embodiment of the present invention.

Examples of biomedical metallic materials usable in the present embodiment include SUS304, SUS316, and like Fe—Cr—Ni alloys; SUS420, SUS440, and like nickel-free stainless steel; Co—Cr alloys, pure titanium, titanium alloys (vanadium-free titanium alloys such as Ti-6Al-4Nb are preferable), etc. Among those, materials which have been subjected to surface treatment such as covering with nitride (TiN), covering with apatite, calcium ion implantation, etc., are preferable.

In particular, a wire obtained by melt spinning a Co—Cr—Mo alloy is particularly preferable as a biomedical metallic material, because it is biocompatible, and has excellent corrosion resistance, wear resistance, processability, and flexibility. As shown in FIG. 1(a), a metallic wire 15 having the above-explained excellent properties can be obtained by spouting molten metal 11 heated by induction heating coils 12 out from a spinning nozzle 2 downwardly, and rapidly solidifying the spouted-out molten metal jet 13 in a liquid coolant layer 14 formed along the inner side of a rotating drum 4. It is preferable that the diameter of the metallic wire 15 be 50-200 μm, and the diameter can be suitably controlled by changing the diameter of the spinning nozzle 2.

An example of a material for the metallic wire is one that comprises 26-31 mass % of Cr, 8-16 mass % of Mo, with the balance being Co and inevitable impurities. From the viewpoint of biocompatibility and in vivo safety, it is preferable that the material does not contain nickel. In order to not adversely affect an MRI (magnetic resonance imaging) apparatus, it is preferable that the material be a non-magnetic biomedical material.

After obtaining a metallic wire formed from a biomedical metallic material, the thus-obtained metallic wire is cut into metallic threads, and a plate-like thread cluster formation step as shown in FIG. 1(b) is then conducted. The length of the cut metallic thread is preferably 1-1000 cm, and more preferably 3-500 cm. In the present embodiment, the length of the metallic thread is about 3-200 cm. In the process of forming a plate-like thread cluster, many metallic threads are dispersed substantially uniformly along a flat surface and temporarily fixed by entangling the metallic threads using equipment for processing fibers into a cotton-like form or felt such as a garnet machine, thread opening machine or hopper feeder. A plate-like thread cluster 6 is thus obtained. The preferable thickness of the plate-like thread cluster 6 is, for example, 3-50 mm.

The plate-like thread cluster is then compressed. Specifically, a plurality of the plate-like thread clusters 6 are formed, laminated as shown in FIG. 1(c), and then compressed as shown in FIG. 1(d) by cold-pressing, etc. The thickness of the compressed laminate is preferably 40-20000 μm.

Subsequently, in FIG. 1(e), a sintering step is conducted. For example, a biomedical porous article 8 composed of sintered plate-like thread clusters is obtained by setting the degree of vacuum of a vacuum-sintering furnace at $2 \times 10^{-3}$ Pa, and conducting vacuum sintering at 1200° C. for 6 hours.

Thereafter, as shown in FIG. 1(f), the biomedical porous article is cut by generating electric discharges between a wire electrode and the biomedical porous article using wire electric discharge machining, etc., so as to have desired dimensions, and thus production of an article 8' is completed. The production method of the biomedical porous article is not limited to those described in the above and it is also possible to obtain an article without a cutting plane by, for example, preparing a mold with desired dimensions in advance, placing the metallic threads in the mold and conducting cold pressing to obtain a plate-like thread cluster having a thickness of 40-20000 μm, and then conducting vacuum sintering in the same manner as described above.

Figure 2:
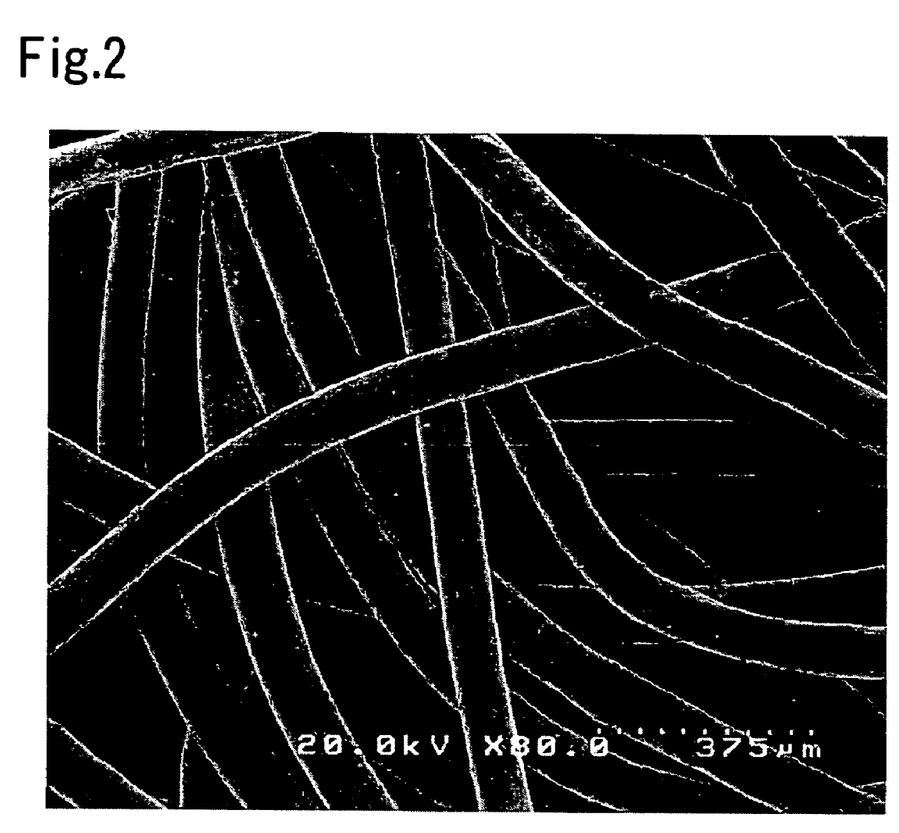
FIG. 2 is an enlarged sectional view of the biomedical porous article.

In the method for manufacturing the biomedical porous article of the present embodiment, since a plate-like thread cluster is formed by dispersing many metallic threads along a flat surface and entangling them, a biomedical porous article having pores three-dimensionally connected can be easily obtained. Therefore, for example, when this biomedical porous article is used as a bone prosthesis, because osseous tissues can easily enter the porous article, the biomedical porous article can be firmly fixed in vivo, and its micromovement can be suppressed. FIG. 2 shows an example of a biomedical porous article obtained by the method of the present embodiment.

The thickness of the compressed plate-like thread cluster laminate can be controlled by changing the compressive load in the compressing step. With taking the thickness of the plate-like thread clusters after compression into consideration, it is possible to easily control the porosity (the proportion of the void (vacancy) volume relative to the apparent volume of the porous article) of the obtained biomedical porous article by suitably adjusting the amount of the metallic thread used. If the porosity of the biomedical porous article is too small, osseous tissues or the like can barely enter the porous article; however too great porosity tends to cause problems with strength. Therefore, the porosity of the biomedical porous article is preferably 10-90%, and more preferably 45-85%.

Figure 3:
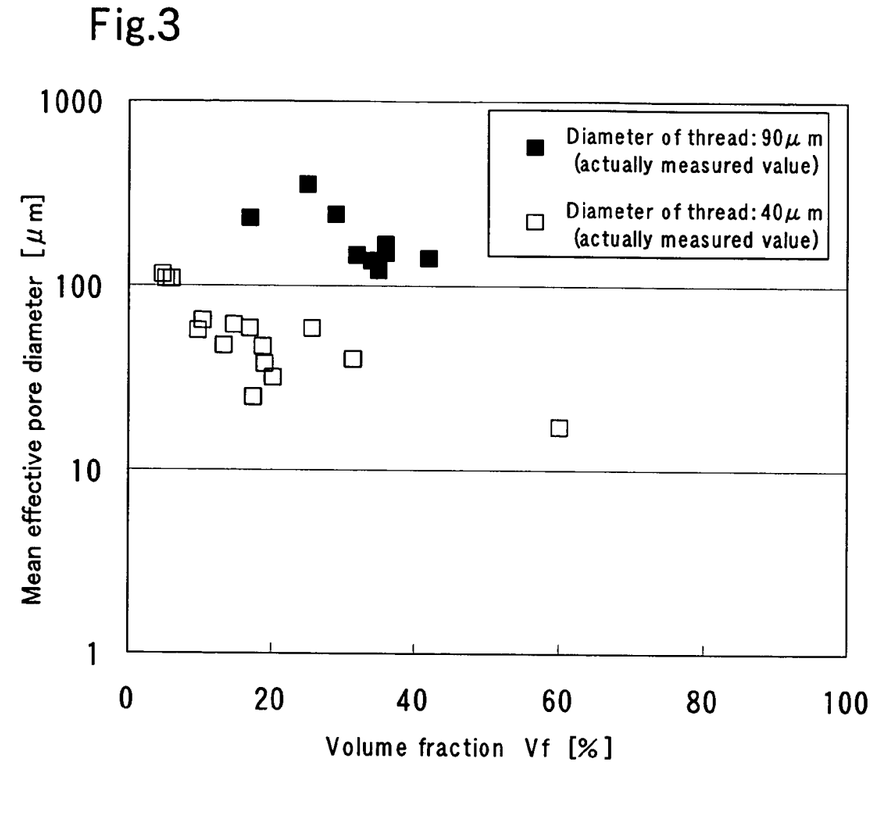
FIG. 3 is a figure showing the relationship between the volume fraction and mean effective pore diameter of the biomedical porous article with using the diameter of a metallic thread as a parameter.

It is possible to control the mean effective pore diameter of the biomedical, porous article to be produced by suitably adjusting the diameter of the metallic thread or the porosity. In other words, as shown in FIG. 3, for a fixed diameter of the metallic thread, the mean effective pore diameter becomes smaller as the volume fraction (100% minus porosity) becomes greater. For a given volume fraction, the mean effective pore diameter becomes greater as the diameter of the metallic thread becomes larger. The mean effective pore diameter of the biomedical porous article may be suitably selected depending on the part of the body where the biomedical porous article to be used, and generally the mean effective pore diameter thereof is preferably 10-1000 μm, and more preferably 100-400 μm. Here the mean effective pore diameter is measured by a half-dry method in accordance with ASTM E1294-89.

It is possible to obtain strength properties suitable for a biomedical porous article by laminating the plate-like thread clusters obtained by dispersing and entangling the metallic threads as described in the present embodiment.

Hard tissues such as bones in a living body have anisotropy wherein their mechanical properties vary depending on the direction from which external force is applied. For example, the strength of a bone against tensile force is clearly different in the vertical axis direction and in the horizontal axis direction as shown by the stress-deformation curves of FIG. 4. Therefore, when a biomedical porous article is used as a bone prosthesis, taking the mechanical properties of bones into consideration, it is preferable that the biomedical porous article have anisotropy corresponding to such properties. Because the biomedical porous article of the present embodiment has a layered structure formed from plate-like thread clusters, its strength differs between the surface direction and the laminating direction. This makes it possible to obtain a biomedical porous article having strength properties corresponding to the mechanical properties of bones.

Figure 5:
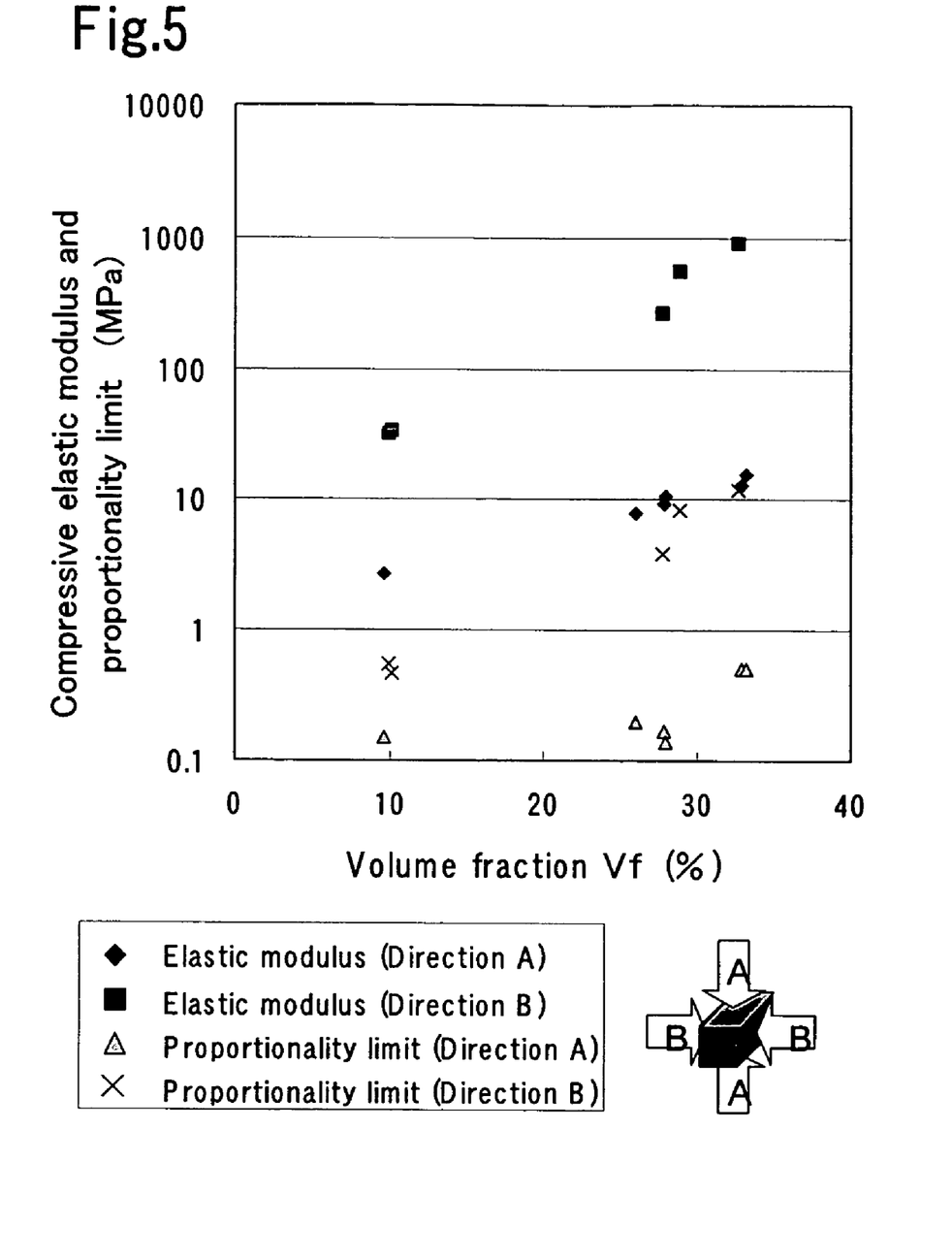
FIG. 5 shows compressive elastic moduli and proportionality limits of the biomedical porous article against a load applied from various directions when the volume fraction of the biomedical porous article is varied.

FIG. 5 is a graph showing the compressive elastic moduli and proportionality limits against compressive loads applied in the laminating direction (Direction A) and side-to-side direction (Direction B) while the volume fraction (Vf) of the biomedical porous article being varied. Co-29Cr-8Mo (mass %) was used as a metallic thread.

As is clear from FIG. 5, when a load is applied in the laminating direction (Direction A), the compressive elastic moduli and proportionality limits are smaller than when a load is applied in the side-to-side direction (Direction B), and therefore the biomedical porous article of the present embodiment clearly has anisotropy. When the volume fraction is varied, the compressive elastic moduli and proportionality limits also change in the both directions, and therefore it is possible to obtain a strength properties preferable for a biomedical porous article by controlling the porosity.

Figure 6:
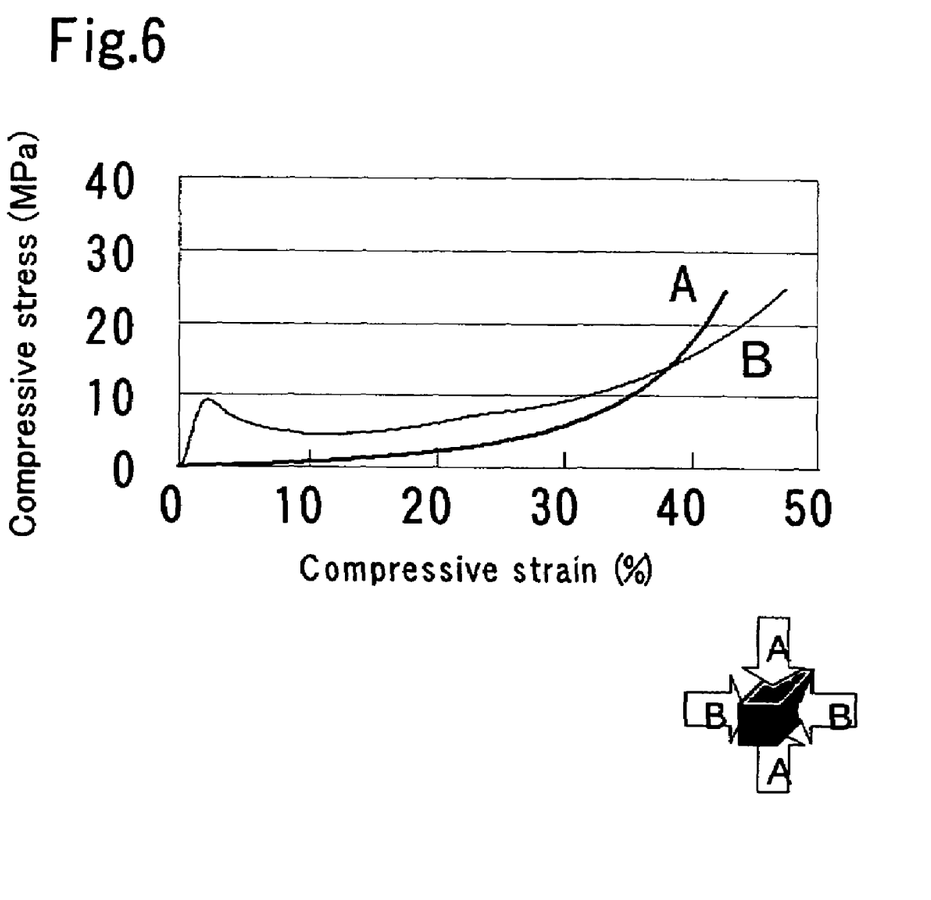
FIG. 6 shows stress-deformation curves of the biomedical porous article against a load applied from various directions.

FIG. 6 is a graph showing stress-deformation curves when loads are applied in the laminating direction (Direction A) and side-to-side direction (Direction B). Co-29Cr-8Mo (mass %) was used as the material for the metallic thread, wherein the volume fraction was about 28% and the compressive deformation rate was 1% $\cdot s^{-1}$.

Figure 4:
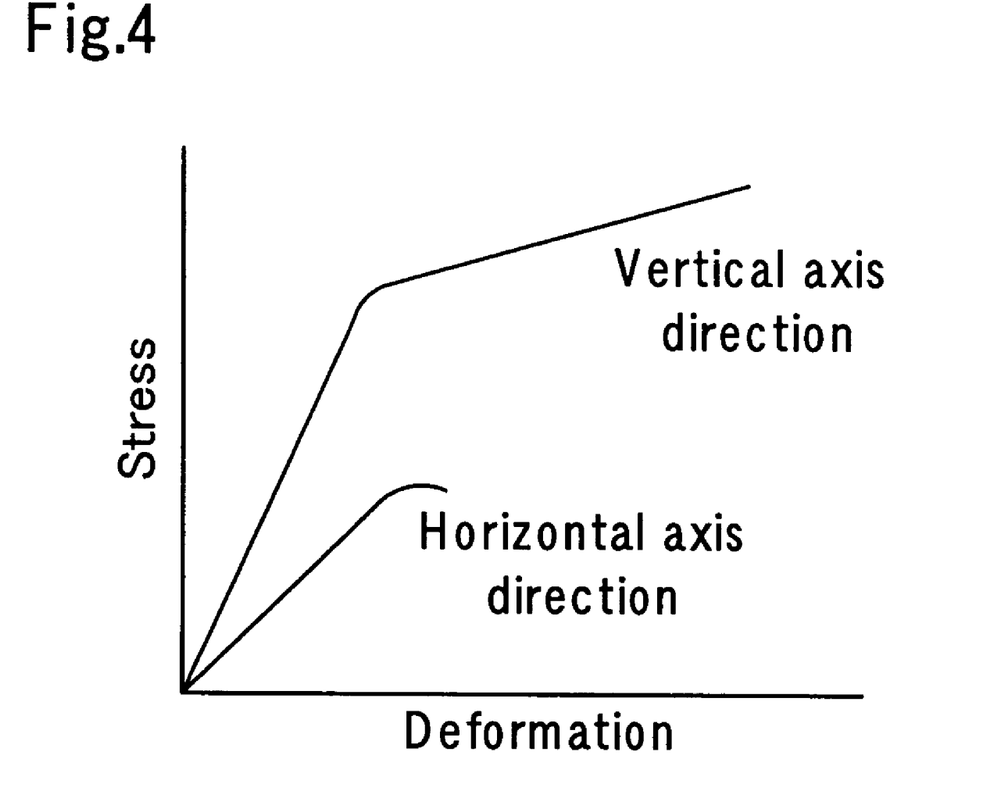
FIG. 4 shows stress-deformation curves of a bone to which a load is applied from various directions.

As is clear from FIG. 6, the stress-deformation curves in both directions are similar to those of the stress-deformation curves of bones as shown in FIG. 4. Therefore, it is clear that the biomedical porous article has desired strength properties.

One embodiment of the present invention is explained in the above; however embodiments of the present invention may be varied depending on the their application, purpose, site of use, etc. For example, the porosities of the laminated plate-like thread clusters may be the same or different. Specifically, it is possible to use plate-like thread clusters having a small porosity (e.g., porosity of 0-10%) in the central portion of the layered structure, and plate-like thread clusters having a relatively large porosity (e.g., porosity of 30-50%) on both sides of the central portion. By using a biomedical porous article thus-formed, it is possible to obtain satisfactory strength while allowing bone and other tissues to easily enter the biomedical porous article.

A plurality of plate-like thread clusters are laminated in the present embodiment; however, it is also possible to obtain a biomedical porous article having a desired porosity and communicability between the pores by compressing and sintering a single plate-like thread cluster.

In the present embodiment, the laminate of the plate-like thread clusters is compressed in the compressing step and then sintered in the sintering step; however, it is also possible to conduct the compressing step and sintering step simultaneously by hot pressing the laminated plate-like thread clusters under vacuum (e.g., at 1200° C. for 6 hours).

Instead of laminating plate-like thread clusters as in the present embodiment, it is also possible to obtain a biomedical porous article by winding belt-like thread clusters into a roll and then sintering. The thus obtained biomedical porous article can have mechanical properties similar to those of bone against bending, compressing, twisting and the like forces, and therefore it can be formed into a biomedical porous article suitable for use as a bone prosthesis. To obtain desired strength properties, the winding strength may be varied in the winding process, for example, tightly winding the central portion to make the volume fraction thereof great, and winding the peripheral portion in a relatively loose manner to make the volume fraction thereof low.

The biomedical porous article thus obtained can be used for a bone prosthesis, specifically, a femoral end component in an artificial hip joint, an pelvic end component in an artificial hip joint, a femoral end component in an artificial knee joint, a tibial end component in an artificial knee joint, a patellal component in an artificial knee joint; an artificial centrum for fixing between centra such as spinal and cervical vertebrae; a spacer between processes, a spacer between ilia, a cranium posterior plate, an internal fixation material for use in treating fracture, an artificial tooth root, and a prosthesis for remedying bone deficiency. Furthermore, the biomedical porous article of the present invention may be used as a percutaneous terminal that is imbedded in vivo, particularly just under the skin, and therefore the biomedical porous article of the present invention is required to closely conform with tissues.

The invention claimed is:

1. A method for manufacturing a biomedical porous article comprising:
 a plate-like thread cluster formation step in which a plate-like thread cluster is obtained by dispersing along a flat surface and entangling many metallic threads made of a biomedical metallic material;
 a compressing step of compressing the plate-like thread cluster into a desired thickness; and
 a sintering step of sintering the plate-like thread cluster;
 wherein the compressing step is conducted in such a manner that a plurality of plate-like thread clusters are laminated and then compressed so as to have a desired total thickness.

2. The method for manufacturing a biomedical porous article according to claim 1, wherein the plurality of plate-like thread clusters include at least two types of plate-like thread clusters of different volume fractions.

3. The method for manufacturing a biomedical porous article according to claim 1, wherein the compressing step and the sintering step are conducted simultaneously in a same step.

4. A method for manufacturing a biomedical porous article comprising:
 a plate-like thread cluster formation step in which a plate-like thread cluster is obtained by dispersing along a flat surface and entangling many metallic threads made of a biomedical metallic material;
 a winding step of winding the plate-like thread cluster into a roll; and
 a sintering step of sintering the wound plate-like thread cluster.

5. A method for manufacturing a biomedical porous article according to claim 1, wherein the metallic thread is formed from a Co—Cr—Mo alloy composed of 26-31 mass % of Cr, 8-16 mass % of Mo, with the balance being Co and impurities, and wherein the metallic thread is obtained from a metallic wire having a diameter of 20-200 μm.

6. A method for manufacturing a biomedical porous article according to claim 4, wherein the metallic thread is formed from a Co—Cr—Mo alloy composed of 26-31 mass % of Cr, 8-16 mass % of Mo, with the balance being Co and impurities, and wherein the metallic thread is obtained from a metallic wire having a diameter of 20-200 μm.

7. The method for manufacturing a biomedical porous article according to claim 1, wherein the metallic thread has a length of 1-1000 cm.

8. The method for manufacturing a biomedical porous article according to claim 4, wherein the metallic thread has a length of 1-1000 cm.

* * * * *

UNITED STATES PATENT AND TRADEMARK OFFICE
CERTIFICATE OF CORRECTION

PATENT NO. : 7,625,519 B2
APPLICATION NO. : 11/104647
DATED : December 1, 2009
INVENTOR(S) : Akihiko Chiba et al.

It is certified that error appears in the above-identified patent and that said Letters Patent is hereby corrected as shown below:

Title Page, Item (73) Assignee

Please change third Assignee from "Kobayashi Pharmaceut Ical Co., Ltd., Osaka-shi (JP)" to --Kobayashi Pharmaceutical Co., Ltd., Osaka-shi (JP)--

Signed and Sealed this
Seventeenth Day of July, 2012

David J. Kappos
*Director of the United States Patent and Trademark Office*